United States Patent
Hutson et al.

(10) Patent No.: US 11,351,095 B2
(45) Date of Patent: Jun. 7, 2022

(54) STABILIZED EMULSIONS WITH ACIDIC AGENTS

(71) Applicant: Avon Products, Inc., Suffern, NY (US)

(72) Inventors: Ashley L. Hutson, Florida, NY (US); Candice DeLeo Novack, Monroe, NY (US)

(73) Assignee: Avon Products, Inc., Suffern, NY (US)

( * ) Notice: Subject to any disclaimer, the term of this patent is extended or adjusted under 35 U.S.C. 154(b) by 0 days.

(21) Appl. No.: 16/439,509

(22) Filed: Jun. 12, 2019

(65) Prior Publication Data
US 2019/0374444 A1 Dec. 12, 2019

Related U.S. Application Data

(60) Provisional application No. 62/683,960, filed on Jun. 12, 2018.

(51) Int. Cl.
*A61K 8/02* (2006.01)
*A61Q 19/00* (2006.01)
*A61K 8/891* (2006.01)
*A61K 8/06* (2006.01)

(52) U.S. Cl.
CPC .......... *A61K 8/0229* (2013.01); *A61K 8/064* (2013.01); *A61K 8/891* (2013.01); *A61Q 19/001* (2013.01)

(58) Field of Classification Search
None
See application file for complete search history.

(56) References Cited

U.S. PATENT DOCUMENTS

| | | | |
|---|---|---|---|
| 6,596,263 B1 | 7/2003 | Schoon et al. | |
| 2004/0258721 A1* | 12/2004 | Bauer | A61K 8/0229 424/401 |
| 2011/0147259 A1 | 6/2011 | Binder et al. | |
| 2015/0164768 A1 | 6/2015 | Novack | |
| 2017/0189278 A1* | 7/2017 | Bchir | A61K 8/895 |

FOREIGN PATENT DOCUMENTS

| | | |
|---|---|---|
| KR | 2018/0037564 A | 4/2018 |
| WO | 2000/56346 A1 | 9/2000 |

OTHER PUBLICATIONS

Konish. Society of Cosmetic Chemists <https://www.scconline.org/wp-content/uploads/2014/10/konish.pdf> Oct. 4, 2014 (Year: 2014).*
PCT/US2019/036835 Search Report—Written Opinion dated Sep. 30, 2019.

* cited by examiner

*Primary Examiner* — Nicole P Babson
(74) *Attorney, Agent, or Firm* — Jonathan D. Ball; Greenberg Traurig, LLP

(57) ABSTRACT

The combination of polyols with certain active ingredients has been found to mitigate the potential irritating nature of some active ingredients (e.g., hydroxy acids, etc.). When applied to lips, this combination may provide for therapeutic and/or cosmetic benefits including smoother lips, increased moisturization, reduced water loss and combinations thereof. However, formulating stable emulsions with certain active ingredients has proved problematic. The present application also provides new stabilization mechanisms for the emulsions involving alteration of the extensional viscosity of the internal phase.

17 Claims, 4 Drawing Sheets

Unhealthy lip surface accentuates lip lines with shadows

Healthy lip surface with reduced lip lines and less shadows

Unhealthy lip surface accentuates lip lines with shadows

Healthy lip surface with reduced lip lines and less shadows

STABILIZED EMULSIONS WITH ACIDIC AGENTS

CROSS REFERENCE TO RELATED APPLICATIONS

This application claims priority to U.S. App. No. 62/683,960, filed Jun. 12, 2018, which is hereby incorporated by reference in its entirety.

FIELD OF INVENTION

The present invention relates to emulsion compositions comprising certain active ingredients. These emulsion compositions are typically glycerin-in-oil and comprise hydroxy acids. The combination of polyols with certain active ingredients has been found to mitigate the potential irritating nature of the active ingredients. When applied to lips, this combination may provide for therapeutic and/or cosmetic benefits including smoother lips, increased moisturization, reduced water loss and combinations thereof. Methods for making these emulsions are also provided.

BACKGROUND OF INVENTION

The skin on the lips is structurally different from skin elsewhere on a human's body. Lips have a thinner stratum corneum and a lesser amount of lipids than non-lip skin or typical skin. This allows water to easily pass through and dissipate from the lips. In fact, water loss through the lips is 10 times greater than water loss through typical skin. This makes the lips more prone to dryness and, over time, to greater damage. Lip stratum corneum also has a high turnover rate, meaning that the corneocytes are constantly shedding. As part of the shedding process, dead cells cluster in flakes on the surface of the lips. When the lips are dry, these flakes are more evident. Due to the variances of lip skin compared to the rest of the body, the thinner stratum corneum combined with a higher rate of cell turnover leaves the lips more susceptible to environmental, mechanical, and chemical assaults. These assaults lead to the feeling of dry, chapped lips and the visual flaking that occurs when lips are damaged beyond the skins natural ability to repair itself.

Accordingly, consumers demand an effective treatment for the lips that moisturizes, heals, and smooths the vulnerable and delicate surface of the lips. Most lip products on the market consist of occlusive oils or waxes that limit the amount of moisture that escapes from the lips. These systems ultimately rely on the skins natural ability to regenerate itself. These products do not address any underlying dryness, and merely prevent further desiccation. Some products also contain moisturizing ingredients and healing ingredients. The efficacy of such products varies widely.

Typically, lipstick products are anhydrous systems. These systems consist of a combination of structurants, emollients, and pigment materials. Lipsticks may also contain between 0.05-3% of a humectant such as glycerin. There have also been instances of emulsion lipsticks typically consisting of a minimum of two phases that are either partially or completely immiscible in each other. Glycerin-in-oil emulsions are of particular interest in the areas of lip and skin as they can provide moisture above and beyond achievable levels found in single phase oleo-based systems. It is well known that emulsions using glycerin in lieu of water in either the continuous or discontinuous phases create a higher level of moisture than can be achieved using water alone.

However, these emulsion lipsticks are often plagued with stability issues. In order to minimize the thermodynamically unfavorable interaction between the phases, due to immiscibility of the phases in an emulsion, there is a tendency for phase separation over time Emulsions are known to undergo phase separation due to destabilization processes such as creaming, flocculation, coalescence, and Ostwald ripening.

Emulsifiers may be used to combat emulsion destabilization. For example, an emulsifier may be chosen specifically for the type of emulsion being used. For systems with low pH in the aqueous phase (or apparent pH where appropriate) several common emulsifiers like PEG-2 stearate and steareth-2 may be used. Thickening of the external phase as related to the internal phase is also known to increase emulsion stability.

However, incorporation of certain actives like α-hydroxy acids into these systems results in increased concentration of electrolytes in the discontinuous phase, which in turn effects the stabilizing mechanism offered by the emulsifier. For example, these electrolytes may destabilize emulsifiers/stabilizers that rely on electrostatic repulsion. However, for some active ingredients, the required pH is too low for standard emulsion stabilizing mechanisms.

Additionally, α-hydroxy acids are not typically applied to the lips due to irritation of the lip skin stemming from low operational pH ranges. This irritation is enhanced in lips as compared to the skin due to the unique structural and morphological characteristics of the lip skin. Formulations containing α-hydroxy acids, such as glycolic and lactic acids, can cause substantial discomfort to some individuals and symptoms of severe skin irritation in others, upon facial application.

Glycerin-in-oil emulsions are particularly sensitive to these changes in the internal phase, where the destabilization and syneresis of the internal glycerin phase to the surface may appear as sweating of the lipstick. This instability can be exacerbated by temperature extremes and by high humidity due to the humectant nature of glycerin. In order to be commercially viable, an emulsion should exhibit sufficient stability through fluctuations in temperature and humidity. However, the stability limitations of glycerin-in-oil have prevented any sort of commercial success.

SUMMARY

It is therefore an object of the invention to provide stable glycerin-in-oil lipsticks comprising one or more α-hydroxy acids. These lipsticks overcome many of the problems previously found with application of certain actives (e.g., α-hydroxy acids) to the skin of lips. It has been found that these lipsticks surprisingly provide increased therapeutic and/or cosmetic benefits as compared to moisturizing lipsticks based on solely on occlusive mechanisms of action or other active ingredients (e.g., vitamin E). The factors afforded by combinations of polyols and certain acidic active ingredients (e.g., α-hydroxy acids, etc.) may align to create a smoother lip surface, increased water retention of the lips, improvement in barrier functionality, thickened stratum corneum, increased moisturizing, and combinations thereof. Moreover, lipsticks of the present invention may have increased stability and therefore the ability to incorporate a wider variety of active ingredients (e.g., α-hydroxy acids, etc.) that do not affect the emulsion stabilization mechanism disclosed herein.

A method of providing therapeutic and/or cosmetic benefit to lips is provided comprising applying a topical emulsion composition comprising glycerin and one or more α-hydroxy acids. In preferred embodiments, the emulsion comprises one α-hydroxy acid and the apparent pH of the glycerin phase is proximal to the $pK_a$ of the α-hydroxy acid. The amount of irritation (or strength of the composition) may be tuned by altering the pH of phases comprising the acid since at a pH near the $pK_a$ in an aqueous system, the acid equilibrium is established with approximately 50% acid and 50% of the corresponding salt of the acid. For example, when the α-hydroxy acid is lactic acid ($pK_a$=3.86) the apparent pH of the glycerin phase may be between 3.3 and 4.3 (e.g., between 3.4 and 4.2, between 3.5 and 4.1, between 3.6 and 4.0, between 3.7 and 3.9, between 3.7 and 4.0, etc.).

In some embodiments, the lip composition may be in the form of an emulsion comprising a glycerin internal phase and one or more α-hydroxy acids. In some embodiments, the glycerin phase has first normal stress value (a marker of the extensional viscosity) of less than 20 Pa (e.g., less than 15 Pa, less than 10 Pa, less than 8 Pa, etc.) at a shear rate of 100 Pa and a temperature of 25° C.

Preferably, the lip composition is in the form of a glycerin-in-oil emulsion comprising one or more α-hydroxy acids.

DETAILED DESCRIPTION

Figure 1:
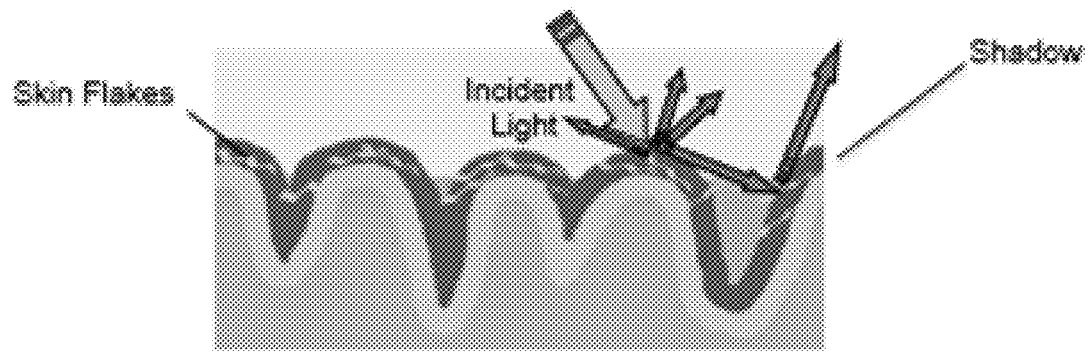
FIG. 1 illustrates the differences in light refraction on healthy and unhealthy lips.
Figure 1:
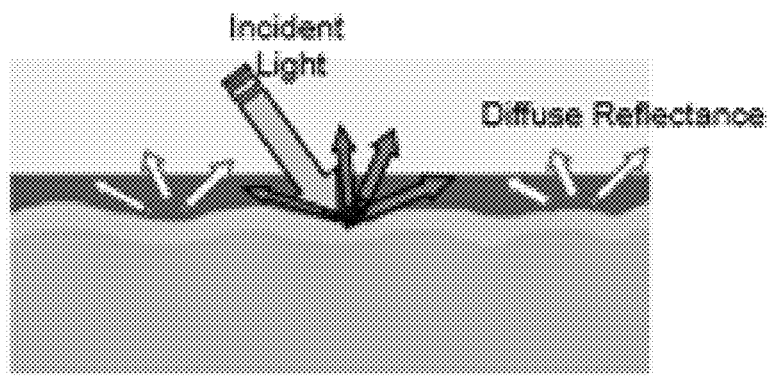

Detailed embodiments of the present invention are disclosed herein; however, it is to be understood that the disclosed embodiments are merely illustrative of the invention that may be embodied in various forms. In addition, each of the examples given in connection with the various embodiments of the invention is intended to be illustrative, and not restrictive.

All terms used herein are intended to have their ordinary meaning in the art unless otherwise provided. All concentrations are in terms of percentage by weight of the specified component relative to the entire weight of the topical composition, unless otherwise defined.

As used herein, "a" or "an" shall mean one or more. As used herein when used in conjunction with the word "comprising," the words "a" or "an" mean one or more than one. As used herein "another" means at least a second or more.

As used herein, all ranges of numeric values include the endpoints and all possible values disclosed between the disclosed values. The exact values of all half integral numeric values are also contemplated as specifically disclosed and as limits for all subsets of the disclosed range. For example, a range of from 0.1% to 3% specifically discloses a percentage of 0.1%, 0.5%, 1%, 1.5%, 2.0%, 2.5%, and 3%. Additionally, a range of 0.1 to 3% includes subsets of the original range including from 0.5% to 2.5%, from 1% to 3%, from 0.1% to 2.5%, etc.

It will be understood that the sum of all weight % of individual components will not exceed 100%.

As used herein, the term "oil" is intended to include silicone oils, unless otherwise noted. The term "oil" is intended to encompass volatile and/or nonvolatile oils. It will be understood that the oil phases of compositions may comprise one or more silicone oils as either the primary or non-primary component of the oil phase.

The terms "internal" and "discontinuous" phase are synonymous, as are the terms "external" and "continuous" phase. The terms "glycerin" and "glycerol" are synonymous and used interchangeably. It will also be understood that water phases of compositions may comprise one or more polyol (e.g., glycerin, etc.) as a non-primary component and polyol (e.g., glycerin, etc.) phases of compositions may comprise water as a non-primary component.

By "proximal to the pKa" in reference to the pH of a phase, it is meant that the phase has a pH near the specified pKa value. In some embodiments, the pH may be within 0.5 pH units of the $pK_a$ (i.e., pH=$pK_a$±0.5), 0.4 pH units of the $pK_a$ (i.e., pH=$pK_a$±0.4), 0.4 pH units of the $pK_a$ (i.e., pH=$pK_a$±0.4), 0.3 pH units of the $pK_a$ (i.e., pH=$pK_a$±0.3), 0.2 pH units of the $pK_a$ (i.e., pH=$pK_a$±0.2), etc.).

The compositions of the invention are useful for application to the skin, lips, nails, hair, and other keratinous surfaces. As used herein, the term "keratinous surface" refers to keratin-containing portions of the human integumentary system, which includes, but is not limited to, skin, lips, hair (including eyebrows and eyelashes), and nails (toenails, fingernails, cuticles, etc.) of mammalians, preferably humans. Preferably, the compositions are applied to the lips.

The compositions are in the form of an emulsion with a polyol and/or aqueous phase. Typically, the emulsions may comprise water and/or glycerin. In some embodiments, the emulsions may be polyol-in-oil, oil-in-polyol, glycerin-in-oil, oil-in-glycerin, silicone-in-glycerin, glycerin-in-silicone, silicone-in-polyol, or polyol-in-silicone emulsions. In preferred embodiments, the emulsion is a polyol-in-oil or glycerin-in-oil emulsion. The emulsions may comprise a non-aqueous external phase (e.g., oil phase, silicone phase, etc.). In some embodiments, the emulsions may comprise an aqueous, a polyol, or a glycerin internal phase.

In certain embodiments, the composition is a polyol-in-oil emulsion comprising a discontinuous, internal polyol (e.g., glycerin, etc.) phase and one or more hydroxy acids (e.g., α-hydroxy acid, β-hydroxy acid, etc.). In most embodiments, the composition is a glycerin-in-oil emulsion. In certain embodiments, the composition comprises a single α-hydroxy acid. In embodiments with a single α-hydroxy acid, the apparent pH of the polyol phase is proximal to the $pK_a$ of that α-hydroxy acid. The internal phase will typically comprise from 1% to 65% by weight of the entire emulsion. More typically, the internal phase will comprise from 5% to 45% by weight of the entire emulsion. The external phase will typically comprise from 25% to 95% (e.g., 55% to 85%) by weight of the entire emulsion.

Suitable polyols for inclusion in the emulsions include, without limitation, $C_{2-6}$ polyols such as ethylene glycol, propylene glycol, butylene glycol, hexylene glycol, sorbitol, diethylene glycol, and glycerin. In most embodiments, the internal phase comprises glycerin. In some embodiments, the polyol phase will comprise glycerin in combination with one or more additional $C_{2-6}$ polyol components. In some embodiments, the polyol phase will further comprise water aside from any water that naturally is absorbed into the polyol phase by it hygroscopic nature.

The active ingredient may be an exfoliating agent. Suitable exfoliating agents include α-hydroxy acids, β-hydroxy acids, keto acids, retinoic acid, lactamides, quaternary ammonium lactates, $C_{4-12}$ hydroxylated carboxylic acids, salicylic acid, and various derivatives thereof. Examples include glycolic acid, lactic acid, citric acid, malic acid, mandelic acid tartronic acid, tartaric acid, glycuronic acid, pyruvic acid, 2-hydroxyalkanoic acid, 2-hydroxyisobutyric acid, 3-hydroxybutyric acid, and derivatives thereof (e.g., esters and reverse esters with alcohols having from one to six carbon atoms like methyl pyruvate). Other active ingredients may include Vitamin $A_2$ (3,4-didehydroretinol), hepaxanthin, (Vitamin A epoxide; 5-6-epoxy-5,6-dihydroretinol) and additional derivative compounds. In certain embodiments, the compositions comprise an α-hydroxy acid. In preferred embodiments, the compositions comprise lactic acid. In some embodiments, the one or more active agents are present in an amount between 0.1 and 20% by weight of the composition (e.g., 0.5% and 10%, 0.5 and 5%, etc.).

Depending on the active ingredient, the apparent pH of the polyol phase or the pH of the aqueous phase may be altered to create less irritating materials from the active ingredient (e.g., conjugate bases of hydroxy acids). For example, the addition of hydroxide salts (e.g., sodium hydroxide, potassium hydroxide, magnesium hydroxide) may be used to change the pH and alter the acid equilibrium balance in the phase. Typically, the polyol has within 0.5 pH units (e.g., within 0.4 pH, within 0.3 pH, within 0.2 pH) of the $pK_a$ of hydroxy acid. In some embodiments, the hydroxide salt is present in an amount between 0.1 and 5% by weight of the composition.

In some embodiments, the external (continuous) phase is an oil phase. For example, the continuous oil phase may comprise any suitable oils for emulsions, including, without limitation, vegetable oils; fatty acid esters; fatty alcohols; isoparaffins such as isododecane and isoeicosane; hydrocarbon oils such as mineral oil, petrolatum, and polyisobutene; polyolefins and hydrogenated analogs thereof (e.g., hydrogenate polyisobutene); natural or synthetic waxes; silicone oils such as dimethicones, cyclic silicones, and polysiloxanes; and the like.

Suitable ester oils include fatty acid esters. Special mention may be made of those esters commonly used as emollients in cosmetic formulations. Such esters will typically be the etherification product of an acid of the form $R_4(COOH)_{1-2}$ with an alcohol of the form $R_5(OH)_{1-3}$ where $R_4$ and $R_5$ are each independently linear, branched, or cyclic hydrocarbon groups, optionally containing unsaturated bonds (e.g., from 1-6 or 1-3 or 1), and having from 1 to 30 (e.g., 6-30 or 8-30, or 12-30, or 16-30) carbon atoms, optionally substituted with one or more functionalities including hydroxyl, oxa, oxo, and the like. Preferably, at least one of $R_4$ and $R_5$ comprises at least 8, or at least 10, or at least 12, or at least 16 or at least 18 carbon atoms, such that the ester comprises at least one fatty chain. The esters defined above will include, without limitation, the esters of mono-acids with mono-alcohols, mono-acids with diols and triols, di-acids with mono-alcohols, and tri-acids with mono-alcohols.

Suitable fatty acid esters include, without limitation, butyl acetate, butyl isostearate, butyl oleate, butyl octyl oleate, cetyl palmitate, cetyl octanoate, cetyl laurate, cetyl lactate, cetyl isononanoate, cetyl stearate, diisostearyl fumarate, diisostearyl malate, neopentyl glycol dioctanoate, dibutyl sebacate, di-$C_{12-13}$ alkyl malate, dicetearyl dimer dilinoleate, dicetyl adipate, diisocetyl adipate, diisononyl adipate, diisopropyl dimerate, triisostearyl trilinoleate, octodecyl stearoyl stearate, hexyl laurate, hexadecyl isostearate, hexyldecyl laurate, hexyldecyl octanoate, hexyldecyl oleate, hexyldecyl palmitate, hexyldecyl stearate, isononyl isononanoate, isostearyl isononanoate, isohexyl neopentanoate, isohexadecyl stearate, isopropyl isostearate, n-propyl myristate, isopropyl myristate, n-propyl palmitate, isopropyl palmitate, hexacosanyl palmitate, lauryl lactate, octacosanyl palmitate, propylene glycol monolaurate, triacontanyl palmitate, dotriacontanyl palmitate, tetratriacontanyl palmitate, hexacosanyl stearate, octacosanyl stearate, triacontanyl stearate, dotriacontanyl stearate, stearyl lactate, stearyl octanoate, stearyl heptanoate, stearyl stearate, tetratriacontanyl stearate, triarachidin, tributyl citrate, triisostearyl citrate, tri-$C_{12-13}$-alkyl citrate, tricaprylin, tricaprylyl citrate, tridecyl behenate, trioctyldodecyl citrate, tridecyl cocoate, tridecyl isononanoate, glyceryl monoricinoleate, 2-octyldecyl palmitate, 2-octyldodecyl myristate or lactate, di(2-ethylhexyl)succinate, tocopheryl acetate, and the like.

Other suitable esters include those wherein $R_5$ comprises a polyglycol of the form H—(O—CHR*—CHR*)$_s$— wherein R* is independently selected from hydrogen or straight chain $C_{1-12}$ alkyl, including methyl and ethyl, as exemplified by polyethylene glycol monolaurate.

The oil may also comprise a volatile or non-volatile silicone oil. Suitable silicone oils include linear or cyclic silicones such as polyalkyl- or polyarylsiloxanes, optionally comprising alkyl or alkoxy groups having from 1 to 10 carbon atoms. Representative silicone oils include, for example, caprylyl methicone, cyclomethicone, cyclopentasiloxane decamethylcyclopentasiloxane, decamethyltetrasiloxane, diphenyl dimethicone, dodecamethylcyclohexasiloxane, dodecamethylpentasiloxane, heptamethylhexyltrisiloxane, heptamethyloctyltrisiloxane, hexamethyldisiloxane, methicone, methyl-phenyl polysiloxane, octamethylcyclotetrasiloxane, octamethyltrisiloxane, perfluorononyl dimethicone, polydimethylsiloxanes, and combinations thereof. The silicone oil will typically, but not necessarily, have a viscosity of between 5 and 3,000 centistokes (cSt), preferably between 50 and 1,000 cSt measured at 25° C.

In one embodiment, the silicone oil comprises phenyl groups, as is the case for a silicone oil such as methylphenylpolysiloxane (INCI name diphenyl dimethicone), commercially available from Shin Etsu Chemical Co under the name including F-5W, KF-54 and KF-56. Diphenyl dimethicones have good organic compatibility and may impart film-forming characteristics to the product. Further, the presence of phenyl groups increases the refractive index of the silicone oil and thus may contribute to high gloss of product if desired. In one embodiment, the silicone oil will have a refractive index of at least 1.3, preferably at least 1.4, more preferably at least 1.45, and more preferred still at least 1.5, when measured at 25° C. Another suitable phenyl-functionalized silicone oil has the INCI name phenyltrimethicone and is sold under the trade name DC 556 by Dow Corning. DC 556 has a refractive index of 1.46. In one embodiment, the silicone oil is a fluorinated silicone, such as a perfluorinated silicone (i.e., fluorosilicones). Fluorosilicones are advantageously both hydrophobic and oleophobic and thus contribute to a desirable slip and feel of the product. Fluorosilicones also impart long-wearing characteristics to a lip product. Fluorosilicones can be gelled with behenyl behenate if desired. One suitable fluorosilicone is a fluorinated organofunctional silicone fluid having the INCI name perfluorononyl dimethicone. Perfluorononyl dimethicone is commercially available from Phoenix Chemical under the trade name PECOSIL®. The compositions may comprise between 5% and 75% silicone oil by weight of the composition (e.g., between 10% and 60% by weight of the composition, between 20% and 50% by weight of the composition, between 25% and 45% by weight of the composition, etc.).

The compositions may also comprise hydrocarbon oils. Exemplary hydrocarbon oils are straight or branched chain paraffinic hydrocarbons having from 5 to 80 carbon atoms, typically from 8 to 40 carbon atoms, and more typically from 10 to 16 carbon atoms, including but not limited to, pentane, hexane, heptane, octane, nonane, decane, undecane, dodecane, tetradecane, tridecane, and the like. Some useful hydrocarbon oils are highly branched aliphatic hydrocarbons, including $C_{8-9}$ isoparaffins, $C_{9-11}$ isoparaffins, $C_{12}$ isoparaffin, $C_{20-40}$ isoparaffins and the like. Special mention may be made of the isoparaffins having the INCI names isohexadecane, isoeicosane, and isododecane.

Also suitable as hydrocarbon oils are poly-α-olefins, typically having greater than 20 carbon atoms, including (optionally hydrogenated) $C_{24-28}$ olefins, $C_{30-45}$ olefins, polyisobutene, hydrogenated polyisobutene, hydrogenated polydecene, polybutene, hydrogenated polycyclopentane, mineral oil, pentahydrosqualene, squalene, and the like. The hydrocarbon oil may also comprise higher fatty alcohols, such as oleyl alcohol, octyldodecanol, and the like.

Other suitable oils include without limitation castor oil, $C_{10-18}$ triglycerides, caprylic/capric/triglycerides, coconut oil, corn oil, cottonseed oil, linseed oil, mink oil, olive oil, palm oil, illipe butter, rapeseed oil, soybean oil, sunflower seed oil, walnut oil, avocado oil, camellia oil, macadamia nut oil, turtle oil, mink oil, soybean oil, grape seed oil, sesame oil, maize oil, rapeseed oil, sunflower oil, cottonseed oil, jojoba oil, peanut oil, olive oil, and combinations thereof.

Any one of the foregoing ester oils, silicone oils, and hydrocarbon oils are contemplated to be useful in the practice of the invention. Accordingly, in one embodiment, the compositions comprise at least one oil selected from the ester oils, silicone oils, and hydrocarbon oils described above. In another embodiment, the compositions comprise two or more oils selected from the ester oils, silicone oils, and hydrocarbon oils described above. In yet another embodiment, the compositions will comprise at least one ester, at least one silicone oil, and at least one hydrocarbon oil from the list above. Because the ester oils described herein function as emollients, it may be advantageous for the compositions to comprise at least one ester oil, and may optionally comprise at least one additional oil selected from hydrocarbon oils, silicone oils, and combinations thereof. For example, in some embodiments, the compositions comprise lanolin, stearyl dimethicone, myristyl lactate, and diphenyl dimethicone.

Waxes and/or fillers may also be optionally added (particularly in those embodiments where the composition is a free standing solid at room temperature), in an amount ranging from at or 1% to or including 20% by weight of the composition or ranging from at or 1% to or including 10% by weight of the composition. Examples of fillers may include, but are not limited to silica, PMMA, nylon, alumina, barium sulfate, or any other filler used in such compositions. Examples of waxes may include, but are not limited to, linear polyethylene, microcrystalline petroleum wax, carnauba wax, lignite wax, ouricouri wax, rice bran wax, castor wax, mortar wax, stearone, acrawax, bayberry wax, castor wax, Japan wax, ozokerite, beeswax, candelilla wax, petrolatum, ceresin wax, cocoa butter, illipe butter, esparto wax, shellac wax, ethylene glycol diesters or tri-esters of $C_{18-36}$ fatty acids, cetyl palmitate, hard tallow, paraffin wax, lanolin, lanolin alcohol, cetyl alcohol, glyceryl monostearate, sugarcane wax, jojoba wax, stearyl alcohol, silicone waxes, and combinations thereof.

In some embodiments, the oil phase can include one or more waxes. Waxes may impart body to the emulsion so that the emulsion has the physical form of a semi-solid or solid. As used herein, the term "solid" is intended to refer to a composition that is self-supporting and capable of being molded into a free-standing stick (e.g., a lip stick). In some embodiments, the waxes are present in an amount sufficient to make the emulsion a solid emulsion. For example, the solid emulsion can have a hardness of at least 30 g. The composition typically has hardness at room temperature of at least 40 g. In one embodiment, the composition may have a substantially greater hardness, between 100 and 300 g. The hardness of an emulsion may be measured on a Texture Analyzer Model QTS-25 equipped with a 4 mm stainless steel probe (TA-24), as described in Avon's U.S. Pat. No. 8,580,283, the disclosure of which is hereby incorporated by reference.

The waxes may be natural, mineral and/or synthetic waxes. Natural waxes include those of animal origin (e.g., beeswax, spermaceti, lanolin, and shellac wax) and those of vegetable origin (e.g., carnauba, candelilla, bayberry, and sugarcane wax). Mineral waxes include, without limitation ozokerite, ceresin, montan, paraffin, microcrystalline, petroleum, and petrolatum waxes. Synthetic waxes include, for example, polyethylene glycols such as PEG-18, PEG-20, PEG-32, PEG-75, PEG-90, PEG-100, and PEG-180 which are sold under the tradename CARBOWAX® (The Dow Chemical Company). Mention may be made of the polyethylene glycol wax CARBOWAX 1000 which has a molecular weight range of 950 to 1,050 and a melting point of 38° C., CARBOWAX 1450 which has a molecular weight range of 1,305 to 1,595 and a melting point of 56° C., CARBOWAX 3350 which has a molecular weight range of 3,015 to 3,685 and a melting point of 56° C., and CARBOWAX 8000 which has a molecular weight range of 7,000 to 9,000 and a melting point of 61° C.

Synthetic waxes also include Fischer Tropsch (FT) waxes and polyolefin waxes, such as ethylene homopolymers, ethylene-propylene copolymers, and ethylene-hexene copolymers. Representative ethylene homopolymer waxes are commercially available under the tradename POLYWAX® Polyethylene (Baker Hughes Incorporated) with melting points ranging from 80° C. to 132° C. Commercially available ethylene-α-olefin copolymer waxes include those sold under the tradename PETROLITE® Copolymers (Baker Hughes Incorporated) with melting points ranging from 95° C. to 115° C.

In one embodiment, the emulsion includes, in the oil phase, at least one wax selected from acrawax (N,N'-ethylenebisstearamide), microcrystalline wax, linear polyethylene wax, stearone (18-pentatriacontanone), castor wax, montan wax, lignite wax, ouricouri wax, carnauba wax, rice bran wax, shellac wax, esparto wax, ozokerite wax, jojoba wax, candelilla wax, ceresin wax, beeswax, castor wax, sugarcane wax, stearyl alcohol, hard tallow, cetyl alcohol, petrolatum, glyceryl monostearate, Japan wax, silicone wax, paraffin wax, lanolin wax, lanolin alcohol, bayberry wax, cetyl palmitate, illipe butter, cocoa butter, and ethylene glycol di- or tri-esters of $C_{18-36}$ fatty acids.

The amount of wax, if present, may be less than 2% (e.g., 0.1-2%) by weight of the composition if the composition is a liquid or if clarity is desired. The amount of wax, if present, will typically be greater than 10% (e.g., 10-20%) by weight of the composition if the composition is a semisolid or solid or if clarity is not a concern. In some embodiments, the emulsion may comprise wax from 1% to 25% or 1-20% or 1-5% or 1-10% by weight of the composition, particularly in embodiments formulated as lip sticks.

The oil phase of the emulsions may also include one or more thickener/gelling agents and/or bulking agents that act as structure-enhancing agents. Such bulking agents include mica, barium sulfate, nylon, talc, starch, calcium carbonate, silica, and mixtures thereof. The bulking agents may be present in an amount of between 0.01% to 5% by weight of the emulsion (e.g., 0.1% to 5% by weight of the emulsion, 0.1% to 1% by weight of the emulsion, etc.).

Other thickeners may be used to thicken either the internal or external phases of the emulsions. For example, polysaccharide thickeners may be used to structure the polyol phase of emulsions as disclosed in US Pub No 2015/0164768, hereby incorporated by reference in its entirety and specifically in relation to polysaccharide structuring agents and emulsifiers. However, since it has been shown that Xanthan gum increases the extensional viscosity of the polyol phase (see Example 2), in preferred embodiments, the composition does not comprise Xanthan gum, or Xanthan gum in such small amounts that the first normal stress difference of the polyol phase is not greater than 20 Pa. In some embodiments, the composition does not have a structurant in the external phase. In some embodiments, the internal phase may be structured with attenuation grade $TiO_2$. The composition may comprise between 0.1% and 20% (e.g., between 0.1% and 10%, etc.) attenuation grade $TiO_2$ by weight of the composition. The attenuation grade $TiO_2$ may be surface treated such as with hydrophobic modifiers including lauroyl lysine, Isopropyl Titanium Triisostearate (ITT), ITT and Dimethicone (ITT/Dimethicone) cross-polymers, ITT and Amino Acid, ITT/Triethoxycaprylylsilane Crosspolymer, waxes (e.g., carnauba), fatty acids (e.g., stearates, etc.), HDI/Trimethylol Hexylactone Crosspolymer, PEG-8 Methyl Ether Triethoxysilane, aloe, jojoba ester, lecithin, Perfluoroalcohol Phosphate, and Magnesium Myristate (MM), to name a few.

In one embodiment, composition includes, in the oil phase, from 0.1-2% or 2-5% or 5-10% or 10-15% or 15-20% by weight of at least one wax (e.g. microcrystalline wax, ozokerite wax, polyethylene wax, paraffin wax, petrolatum wax, etc.). In one embodiment, the composition includes, in the oil phase, microcrystalline wax within the foregoing amounts. In one embodiment, the composition includes, in the oil phase, ozokerite wax within the foregoing amounts. In one embodiment, the composition includes, in the oil phase, polyethylene wax within the foregoing amounts. In one embodiment, the composition includes, in the oil phase, petrolatum wax within the foregoing amounts. In one embodiment, the composition includes, in the oil phase, paraffin wax within the foregoing amounts.

Typically, emulsions according to the invention further comprise one or more emulsifiers. For example, the one or more emulsifiers may be present in a total range from 0.01% to 20.0% by weight of the emulsion (e.g., from 0.1% to 15% by weight of the emulsion). In some embodiments, the total amount of emulsifier ranges from 0.1% to 6.0% be weight, or from 0.5% to 4.0% by weight of the emulsions. Examples of emulsifiers include polyglyceryl compounds such as polyglyceryl-6-polyricinoleate, polyglyceryl pentaoleate, polyglyceryl-isostearate, and polyglyceryl-2-diisostearate; glycerol esters such as glycerol monostearate or glycerol monooleate; phospholipids and phosphate esters such as lecithin and trilaureth-4-phosphate (available under the tradename HOSTAPHAT®KL-340-D); sorbitan-containing esters (including SPAN® esters) such as sorbitan laurate, sorbitan oleate, sorbitan stearate, or sorbitan sesquioleate; polyoxyethylene phenols such as polyoxyethylene octyl phenol; polyoxyethylene ethers such as polyoxyethylene cetyl ether and polyoxyethylene stearyl ether; polyethylene glycol emulsifiers such as PEG-30-polyhydroxystearate or alkylpolyethylene glycols; polypropylene glycol emulsifiers such as PPG-6-laureth-3; dimethicone polyols and polysiloxane emulsifiers; and the like. Combinations of emulsifiers, such as the combination of lecithin and sorbitan, are envisioned. Additional emulsifiers are provided in the INCI Ingredient Dictionary and Handbook, 12th Edition, 2008, the disclosure of which is hereby incorporated by reference. In some embodiments, the lip composition comprises one or more emulsifiers and/or one or more waxes. In preferred embodiments, the lip composition comprises between 1% and 20% emulsifiers and/or between 1% and 20% waxes by weight of the composition.

In some embodiments, the compositions may require increased stability not available with standard emulsification systems. Methods of increasing stability of polyol-in-oil emulsions are also provided comprising decreasing the extensional viscosity of the glycerin phase of said emulsion. As a proxy for extensional viscosity, the first normal stress difference of the internal phase may be determined at a shear rate of 100 Pa and a temperature of 25° C. A higher first normal stress difference correlates with a higher extensional viscosity. It has been found the stability of polyol-in-oil emulsions may be increased by decreasing the extensional viscosity of the internal phase. In some embodiments, the polyol (e.g., glycerin) phase has first normal stress difference of less than 20 Pa at a shear rate of 100 Pa (e.g., less than 15 Pa, less than 10 Pa, less than 8 Pa, less than 7 Pa, less than 6 Pa) and a temperature of 25° C.

Composite elastomeric powders may be included to increase the stability of solid emulsions and to decrease the syneresis over long storage periods. Examples of elastomeric powders include silicone elastomers which are cross-linked flexible silicones that can undergo large reversible deformations. In some embodiments, the extensional viscosity is decreased by the addition of a silicone elastomer to the discontinuous phase of the emulsions. The silicone elastomer may be, for example, a crosslinked elastomeric organopolysiloxane powder including dimethicone crosspolymer. Such elastomers may be formed, for example, by platinum metal catalyzed reactions between SiH containing diorganopolysiloxanes and organopolysiloxanes having silicon bonded vinyl groups. Suitable silicone elastomers include dimethicone/vinyl dimethicone crosspolymers, vinyl dimethicone/methicone silsesquioxane crosspolymers, and dimethicone/phenyl vinyl dimethicone crosspolymers. Examples include Dow Corning 9040, 9041, and 9506, and Shin-Etsu KSG-15, 16, and 17, and Shin-Etsu KSP-100, 101, 102, 103, 104, 105, 200 and 300. Commercially available powders include Dow Corning 9506 Powder from the company Dow Corning (INCI name: Dimethicone/vinyl dimethicone crosspolymer). In particular, the organopolysiloxane elastomer used in the present invention is chosen from Dimethicone Crosspolymer (INCI name), Dimethicone (and) Dimethicone crosspolymer, Vinyl Dimethicone Crosspolymer (INCI name), Dimethicone/Vinyl Dimethicone Crosspolymer (INCI name), Dimethicone Crosspolymer-3 (INCI name), and in particular Dimethicone crosspolymer and Dimethicone (and) Dimethicone crosspolymer.

Composite elastomeric powders may be formed by coating at least a portion of the particles of the elastomeric powder with an inorganic powder. Typically, the inorganic powder has an average particle size less than the average particle size of the uncoated elastomeric powder. Typically, the average particle size of the coating inorganic powder particles is less than one tenth of the average particle size of the uncoated elastomeric powder. Examples of suitable inorganic powders for creation of the composite elastomeric powder include metal oxide powders such as silicon oxide, titanium oxide, aluminum oxide, zirconium oxide, antimony oxide; metal nitride powders such as boron nitride, and aluminum nitride; metal hydroxide powders such as aluminum hydroxide, magnesium hydroxide; metal carbonate salts such as potassium carbonate; metals such as nickel, cobalt, iron, copper, gold, and silver; sulfide powders; and chloride powders. Preferred powders for coating of the elastomeric particles include metal oxide fine powders and specifically silica. Suitable composite elastomeric particles include Dow Corning 9701 Powder from the company Dow Corning (INCI name: Dimethicone/vinyl dimethicone crosspolymer (and) silica).

Typically, the composite elastomeric particle may be coated with a component to impart hydrophilicity and dispersibility to the composite elastomeric particles. This is particularly important in glycerin-in-oil emulsions where the composite particles may be dispersed throughout the glycerin-in-oil phase. In some embodiments, the composite elastomeric particle comprises a monohydric alcohol such as methanol, ethanol, isodecyl alcohol, isotridecyl alcohol and/or polyhydric alcohols including glycols such as 1,3-butanediol, 1,2-pentanediol, ethylene glycol, dipropylene glycol and the like. In some embodiments, the composite elastomeric particle is coated with butylene glycol. Such composite elastomeric particles are described in U.S. Pat. No. 9,394,412, hereby incorporated by reference in its entirety and specifically in relation to composite cured silicone powders. In preferred embodiments, the composite elastomeric particles include the product sold by the company Dow Corning under the name EP-9801 Hydrocosmetic Powder (INCI name: Dimethicone/vinyl dimethicone crosspolymer (and) silica (and) butylene glycol).

In some embodiments the composition may be a polyol-in-oil (e.g., glycerin-in-oil) emulsion and comprise between 1% and 45% polyol (e.g., between 1% and 20%, between 5% and 15%) by weight of the composition, and between 0.1% and 5% active ingredient (e.g., α-hydroxy acid like lactic acid), and between 25% and 95% (e.g., between 40% and 60%) oil (e.g., lanolin, stearyl dimethicone, myristyl lactate, diphenyl dimethicone, and combinations thereof) by weight of the composition. In some embodiments, the composition further comprises a hydroxide salt (e.g., sodium hydroxide) in an amount between 0.1 and 5% by weight of the composition.

Additional components may be incorporated for various functional purposes as is customary in the cosmetic arts into the composition, and specifically the internal phase of emulsions, the external phase of emulsions, or as a particulate phase. However, while additional components consistent to formulate the above cosmetic compositions may be included, the inclusion of additional ingredients is limited to those ingredients in amounts which do not interfere with the formation or stability of the compositions (e.g., emulsions, etc.).

Such components may be selected from the group consisting of film-formers, pigments, waxes, emollients, moisturizers, preservatives, flavorants, antioxidants, botanicals, and mixtures thereof. Particular mention may be made of highly purified botanical extracts or synthetic agents which may have wound-healing, anti-inflammatory, or other benefits useful for treating the skin or lips. Additional embodiments may include antioxidants such as tocopherol and/or α-hydroxy acids like glycolic acid, lactic acid, etc. The compositions may include one or more film-formers to increase the substantivity of the product.

Film formers, including film forming polymers, may also be employed. The term film-forming polymer may be understood to indicate a polymer which is capable, by itself or in the presence of at least one auxiliary film-forming agent, of forming a continuous film which adheres to a surface and functions as a binder for the particulate material. Polymeric film formers include, without limitation, acrylic polymers or co-polymers, (meth)acrylates, alkyl(meth)acrylates, polyolefins, polyvinyls, polacrylates, polyurethanes, silicones, polyamides, polyethers, polyesters, fluoropolymers, polyacetates, polycarbonates, polyamides, polyimides, rubbers, epoxies, formaldehyde resins, organosiloxanes, dimethicones, amodimethicones, dimethiconols, methicones, silicone acrylates, polyurethane silicones copolymers, cellulosics, polysaccharides, polyquaterniums, and the like. Suitable film formers include those listed in the Cosmetic Ingredient Dictionary (INCI and Handbook, 12th Edition (2008)), the disclosure of which is hereby incorporated by reference.

The composition may comprise one or more preservatives or antimicrobial agents, such as methyl, ethyl, or propyl paraben, and so on, in amounts ranging from 0.0001-5 wt % by weight of the total composition. The compositions may have other ingredients such as one or more anesthetics, anti-allergenics, antifungals, anti-inflammatories, antimicrobials, antiseptics, chelating agents, emollients, emulsifiers, fragrances, humectants, lubricants, masking agents, medicaments, moisturizers, pH adjusters, preservatives, protectants, soothing agents, stabilizers, sunscreens, surfactants, thickeners, viscosifiers, vitamins, or any combinations thereof.

In one embodiment, the emulsions according to the invention are provided as products for application to the lips. Such lip products may include lip cream, lip balm, lip gloss, medicated lip treatment, lip moisturizer, lip cosmetic, lip sunscreen, and lip flavorant. In one embodiment, the lip product is a creamy, flowable lip product. In certain embodiments, products according to the invention may have the consistency of a semi-viscous liquid or paste. In other embodiments, the product is a lipstick.

Application of these compositions to keratinous surfaces confers therapeutic and/or cosmetic benefits. Methods are also provided for providing the therapeutic and/or cosmetic benefits to lips found only by the combination of polyols and exfoliating actives described herein. In some embodiments, the therapeutic and/or cosmetic benefit is selected from a reduction in water loss from said lips, smoother lip surface (as compared to untreated lips), increased moisture of said lips (as compared to untreated lips), increased barrier function of said lips (as compared to untreated lips), thickened stratum corneum of said lips (as compared to untreated lips), and combinations thereof.

The amount of the topical composition applied each time, the area of application, the duration of application, and the frequency of application may vary widely, depending on the specific need of the user. For example, the topical composition may be applied for a period of at least one month and at a frequency ranging from once per week or twice per week or twice a week or every other day or once per day or two times a day (e.g., once in the morning and once at night, etc.) or three times a day or four times a day or five times a day. In some embodiments, one composition form (e.g., a lipstick of the invention) may be applied during one or more times (e.g., one, two, three, four, five, etc.) throughout and another composition form (e.g., a balm of the invention) may be applied and left on overnight while the user sleeps.

In most embodiments, the compositions are packaged singularly in their own container. In one embodiment, one or more compositions are each contained in separate containers and multiple single-formula containers (for example, jars and dispensers) are sold and/or packaged together (e.g., lipstick and balm). In another embodiment, multiple compositions (e.g. lipstick, balm, cream, etc.) are contained in different reservoirs in the same package. In some embodiments, these different reservoirs are not separable from one another.

EXAMPLES

The following examples illustrate specific aspects of the instant description. The examples should not be construed as limiting, as the example merely provides specific understanding and practice of the embodiments and its various aspects.

Example 1: Measurement of Moisture Content and Trans Epidermal Water Loss of Lips An eight-week clinical study of various formulations applied to lips was conducted. Women with rough lips, ages 40-65 and skin types I-III on the Fitzpatrick scale, applied a specific lipstick composition at least 3 times a day. Several groups were instructed to also apply a balm at night. The specifics of the formulations are shown in Table 1. As can be seen, Formulation 1 is a glycerin-in-oil emulsion comprising α-hydroxy acids and Formulation 2 is a gelled composition comprising a lower glycerin content and no α-hydroxy acid. Additionally, another group of participants was instructed to apply the commercially available Intense Lipstick by oBoticário. This Intense Lipstick moisturizes the lips based on water occlusion in combination with vitamin E and Cupuaçu butter. Each group between 9 and 11 participants.

TABLE 1

| Component | Formulation 1 (wt %) | Formulation 2 (wt %) | Balm (wt %) |
|---|---|---|---|
| Oil (e.g., lanolin, stearyl dimethicone, myristyl lactate, diphenyl dimethicone, squalene, diisostearyl fumarate, polybutene, or combinations thereof) | 50.11 | 55.67 | 52.45 |
| Glycerin | 10.00 | 1.50 | 10.00 |
| α-hydroxy acid (Lactic Acid) | 2.00 | — | 2.00 |
| Base (Ammonium Hydroxide 30%) | 0.35 | — | 0.35 |
| Emulsifier (e.g., laurylmethicone copolyol, polyglyceryl-3 diisostearate, and combinations thereof) | 8.75 | — | 8.75 |
| Dimethicone/Vinyl Dimethicone Crosspolymer, Silica, and Butylene Glycol (EP-9801) | 3.00 | — | 3.00 |
| Other Powders (e.g., polyethylene 12 micron, acrylate copolymer E603, lauryl methacrylate/glycol dimethacrylate cross polymer, fumed silica, mica, or combinations thereof) | 2.63 | 2.83 | 2.63 |
| Preservative | 0.50 | 0.50 | 0.50 |
| Demineralized Water | 1.00 | — | 1.00 |
| Active Ingredients (e.g., sunscreen, sweetener, antioxidant, skin protectant, skin conditioner, protein, and combinations thereof) | 7.91 | 13.70 | 7.91 |
| Gellant | — | 2.90 | — |
| Bulking Agent (e.g., barium sulfate) | — | 0.40 | 2.66 |
| Wax | 8.75 | 13.40 | 8.75 |
| Colorants (e.g., pigments, lakes, dyes, or combinations thereof) | 5.00 | 9.10 | — |

At one (1) week, two (2) weeks, four (4) weeks and eight (8) weeks, the hydration and barrier function of the lips (without product on) was assessed by measurement of skin capacitance and Trans Epidermal Water Loss ("TEWL"). The health of the lips was also assessed by optical measurement of the glossiness of lips. In the images, it could be seen that, incident light on unhealthy lips with increased skin flakes and a non-uniform surface tends to create accentuate lines with shadows. On healthy lips, the lack of these features mitigates the presence of these shadows. A schematic of the mechanism causing this distinction between healthy and unhealthy lips is provided in FIG. 1. Additionally, regression period measurements were performed following the eight week study. At 24 hours and 72 hours after conclusion of the application phase of the study, the skin capacitance and TEWL of participants were again measured. Participants did not wear any lip products during the regression time periods.

Figure 2A:
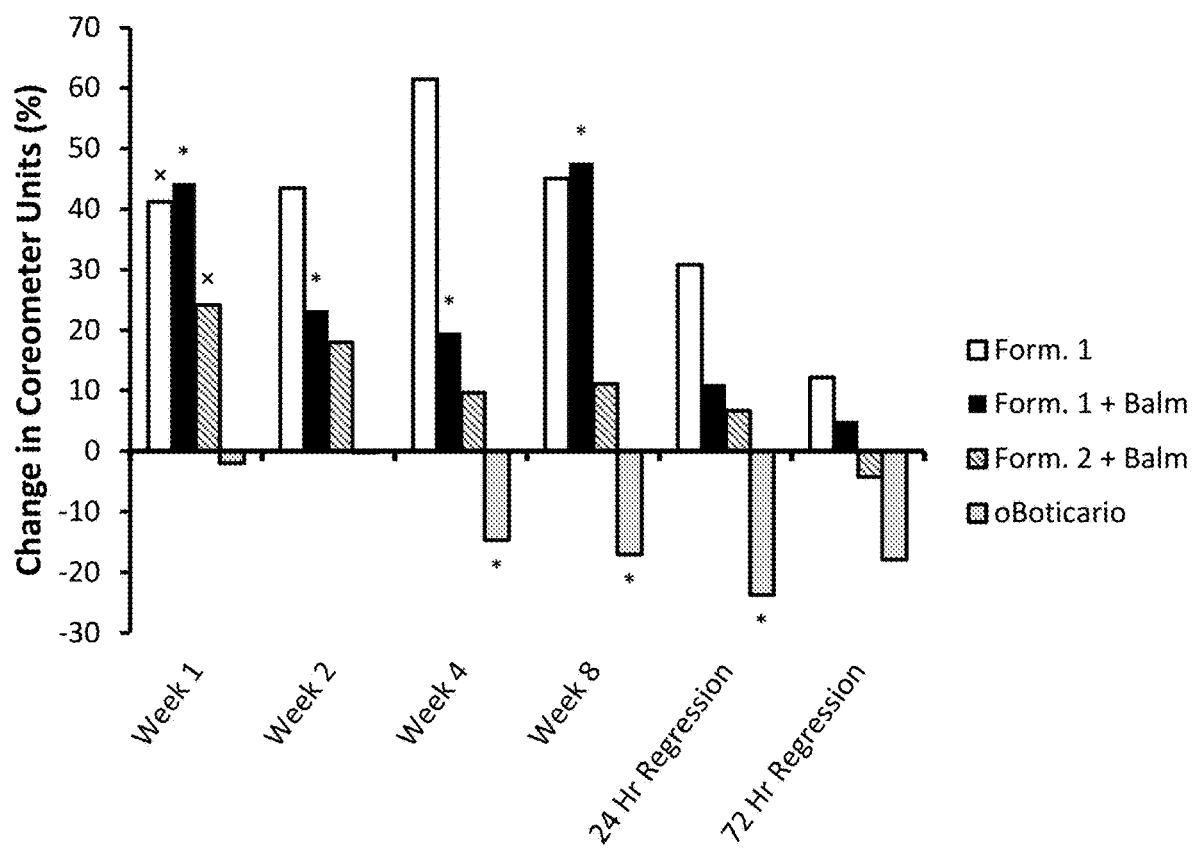
FIG. 2A shows the average percentage change in corneometer readings for each sample population of the clinical study. "*" represents statistically significant results with respect to measurement on the lips at the beginning of the study with a significance of p≤0.05, while "x" represents those results with a statistical significance of p≤0.10.

The Corneometer (Courage & Khazaka) quantifies moisture content of the lips using an electrical capacitance measurement at the surface of the lips. By measuring the electrical capacitance at the surface of the lips, a measurement of the lip water content is acquired due to differences in the dielectric constant of water and other substances. Higher corneometer units are indicative of higher moisture content in the lips. Measurements were taken on lips without product thereon. FIG. 2A shows the results for the corneometer measurements for each tested population at various time points.

Figure 2B:
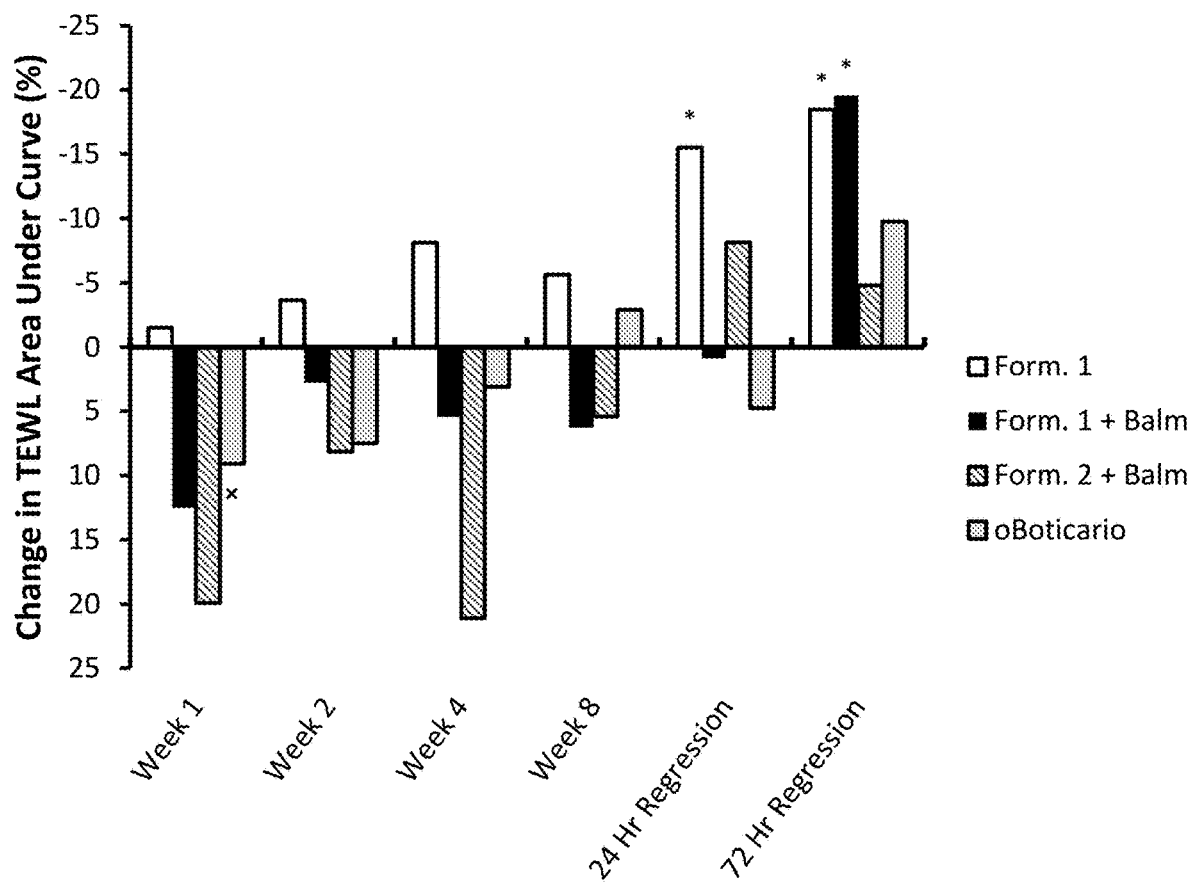
FIG. 2B shows the average percentage change in TEWL measurements for each sample population of the clinical study.

TEWL measurements taken with a Ventilated Chamber Evaporimeter (cyberDERM) reflected the water loss from the lip epidermis at each time point. Measurements were taken on lips without product thereon. A defective barrier results in higher water loss while lower TEWL values indicates the prevention of water loss. FIG. 2B shows the results of the TEWL measurements for each tested population at the various time points, on an inverted y-axis.

Figure 2C:
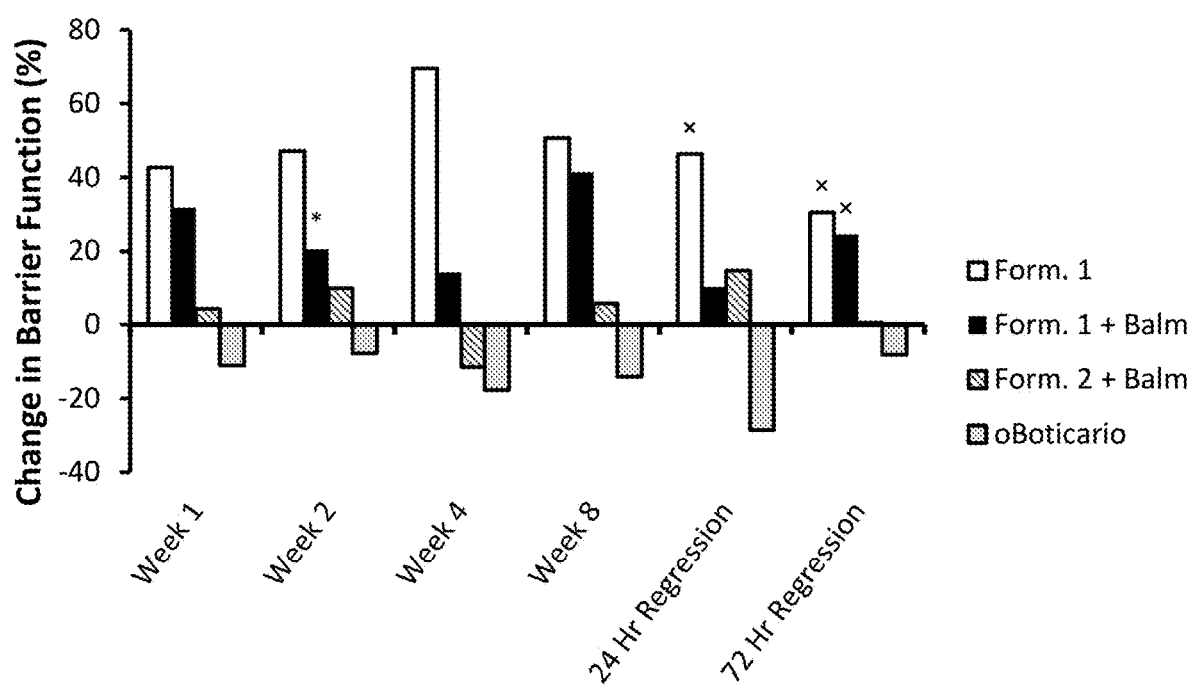
FIG. 2C shows the average percentage change in barrier function for each sample population of the clinical study.

The amount of water lost by lips is impacted not only by barrier, by the amount of moisturization in the lips. A full picture of the barrier function change for the lips of each sample population was calculated by subtracting each subject's percent change in TEWL from the percent change in skin capacitance. FIG. 2C shows the change in barrier function for each sample population. In FIGS. 2A-2C "*" represents statistically significant results with respect to measurement on the lips at the beginning of the study with a significance of $p \leq 0.05$ (two-tailed distribution), while "x" represents those results trending towards significance at $p \leq 0.10$ (two-tailed distribution).

The optical measurements showed that those populations receiving glycerin- and α-hydroxy acids had healthier, smoother lips. Moreover, as can be seen in FIGS. 2A-2C, treatment with formulations comprising glycerin and α-hydroxy acids were able to significantly increase moisturization of the lips and a statistically significant reduction in water loss on the bare skin. In fact, only those subjects using treatments comprising daily multiple treatments of glycerin and α-hydroxy acid had significantly less water loss after three days of regression. Moreover, these results are not seen in the commercially available moisturizing Intense Lipstick which operates by occlusion in combination with vitamin E and Cupuacu butter. The combination α-hydroxy acid and glycerin uniquely provides a smoother lip surface, delivers moisture to the lips, and reduces water loss of the lips.

Example 2: First Normal Stress Measurements on Glycerin Phases with α-Hydroxy Acids The first normal stress difference of several glycerin phases ("Phase") was measured prior to emulsification. The components of these glycerin phases are shown in Table 2.

TABLE 2

|  | Phase A (g) | Phase B (g) | Phase C (g) | Phase D (g) | Phase E (g) |
|---|---|---|---|---|---|
| Glycerin | 93.60 | 93.60 | 93.60 | 93.60 | 93.60 |
| Lactic Acid | — | 2.00 | 2.00 | 2.00 | 2.00 |
| Demineralized Water | — | — | — | 1.00 | 1.00 |
| Ammonium Hydroxide, 30% | — | — | 0.40 | 0.40 | 0.40 |
| Dimethicone/Vinyl Dimethicone Crosspolymer/Silica/Isoceteth-10/BG/Antiox. | — | — | — | — | 3.00 |
| Xanthan Gum | 1.00 | — | — | — | — |
| Total Weight | 94.60 | 95.60 | 96.00 | 97.00 | 100.00 |

A TA Instruments AR-G2 Rheometer was used to perform viscosity measurements for each of the phases A-E and a 100% glycerin phase using a 2 degree cone and plate geometry and a 52 micron gap. Measurements were taken at a shear stress of 100 Pa and 25° C. (77° F.). To understand the extensional viscosity trend among the Phases in Table 2, the first normal stress difference may calculated using $N_1 = 2 \times J_e \times \eta^2 \times \dot{\gamma}^2$, wherein $J_e$ is the recoverable compliance, $\eta$ is the viscosity, and $\dot{\gamma}$ is the shear rate as measured by the rheometer. The first normal stress differences for each tested glycerin phase and a 100% glycerin phase are shown in Table 3.

TABLE 3

|  | Glycerin (100%) | Phase A | Phase B | Phase C | Phase D | Phase E |
|---|---|---|---|---|---|---|
| First Normal Stress Difference ($N_1 = 2 \times J_e \times \eta^2 \times \dot{\gamma}^2$, Pa) | 0 | 1315.9 | 164.0 | 0 | 29.6 | 5.7 |

A larger first normal stress difference is indicative of a higher extensional viscosity. As can be seen, 100% glycerin has no extensional viscosity. However, the addition of various components to the glycerin phase like Xanthan gum, lactic acid ammonium hydroxide, and water result in increases to the extensional viscosity of the glycerin system. The incorporation of various silicone elastomer like Dimethicone/Vinyl Dimethicone Crosspolymer/Silica/Butylene Glycol (EP-9801 available from Dow Corning) may decrease the extensional viscosity of the internal phase.

Example 3: Stability Measurements on Glycerin-in-Oil Emulsions

Glycerin-in-oil emulsions were prepared to illustrate the stability of emulsions prepared with various α-hydroxy acids and composite elastomeric polymers. Table 4 illustrates the components of Formulations 3-7 tested in the stability measurements.

TABLE 4

|  | Form. 3 (wt. %) | Form. 4 (wt. %) | Form. 5 (wt. %) | Form. 6 (wt. %) | Form. 7 (wt. %) |
|---|---|---|---|---|---|
| Lactic Acid | 2.00 | 2.00 | 2.00 | 2.00 | 2.00 |
| Base | 0.35 | 0.40 | 0.40 | 0.35 | 0.35 |
| Conditioning agent | 1.00 | 1.00 | 1.00 | 1.00 | 1.00 |
| Oil | 51.32 | 54.92 | 52.57 | 53.32 | 48.62 |
| Emulsifier | 0.00 | 0.00 | 0.00 | 0.00 | 0.00 |
| Glycerin | 10.00 | 10.00 | 10.00 | 10.00 | 10.00 |
| Water | 1.00 | 1.00 | 1.00 | 1.00 | 1.00 |
| Cellulose Beads | 5.00 | 0.00 | 0.00 | 0.00 | 0.00 |
| Composite Elastomeric Particle (EP-9801) | 0.00 | 1.00 | 2.00 | 3.00 | 5.00 |
| Wax | 4.13 | 8.83 | 8.83 | 7.13 | 11.83 |
| Additional Ingredients† | 15.83 | 19.03 | 18.03 | 15.83 | 18.53 |

†Additional ingredients may include fragrance oil, pigments, other powders, preservatives, sunscreen active, sweetener and combinations thereof.

As can be seen, Formulations 3-7 were prepared without emulsifiers thus allowing for the stability effect provided by the composite elastomeric particle to be shown. The conditioning agent used in these formulations, a hybrid polymer comprising a silk protein, silicone and an alkyl group (Protosil LH available from SEPPIC), may provide some emulsion stability. However, Formulation 3, the formulation without any composite elastomeric particle, was unstable as an emulsion and could not undergo further experimentation since conditioning agent was insufficient to stabilize the emulsion. Formulations 4-7 were allowed to solidify into stick form for further stability testing.

Sticks were placed in several environments (77° F., 40° F., alternating 40° F. (12 hours) and 110° F. (12 hours), 120° F., and 120° F. with 90% humidity) for four weeks. Following four weeks in each environment, observable changes to the stick were noted and ranked from zero (0) to five (5) dependent on visible changes to the stick (e.g., syneresis). A zero represents no observable change and a five represents a critically observable change indicative of instability of the formulation. Table 5 summarizes the observable changes in each of the sticks after four weeks in each environment.

TABLE 5

|  | Form. 4 | Form. 5 | Form. 6 | Form. 7 |
| --- | --- | --- | --- | --- |
| % Composite Elastomeric Particle | 1.00 | 2.00 | 3.00 | 5.00 |
| 77° F. | 0 | 0 | 0 | 0 |
| 40° F. | 0 | 0 | 0 | 0 |
| 40° F./110° F. | 2 | 2 | 1 | 1 |
| 120° F. | 5 | 2 | 0 | 0 |
| 120° F. (90% Humidity) | 5 | 5 | 3 | 1 |
| Freeze/Thaw Cycles | 0 | 0 | 0 | 0 |

As can be seen, increasing the amount of composite elastomeric particle in the compositions increased the stability of the glycerin-in-oil emulsions. Emulsions ranged from complete instable (Formulation 3) to minimal syneresis observed in even severe conditions (Formulations 6 and 7). For example, the glycerin-in-oil emulsion with 5% elastomer powder was the most stable formulation in the 120° F. (90% humidity) environment.

Similar stability measurements were performed on compositions with other α-hydroxy acids formulated therein. Glycerin-in-oil emulsions were prepared with emulsifiers (polyglyceryl-3 diisostearate and lauryl methicone) and either 2% lactic acid by weight, 2.43 glycolic acid by weight, or 1.89% trioxaunedecanedioic acid by weight. In the 120° F. (90% humidity) environment the lactic acid formulation had a stability measurement of 1 after four weeks, the glycolic acid formulation had a stability measurement of 3 with some discoloration of the stick, and the trioxaunedecanedioic acid formulation was unable to set as a solid stick. As can be seen, the exact α-hydroxy acid used in the emulsion has an effect on the stability of the glycerin-in-oil emulsion. However, stable glycerin-in-oil emulsions of various α-hydroxy acids other than lactic acid may be formulated with known means including the use of different emulsification systems, alterations of viscosities of the internal phase, etc. Moreover, incorporation of different amounts of the composite elastomeric particle into these formulations may also increase the stability of the emulsions.

SPECIFIC EMBODIMENTS

Specific embodiments of the present disclosure are enumerated below.

Specific Embodiment 1

A lip composition in the form of a glycerin-in-oil emulsion comprising one or more α-hydroxy acids.

Specific Embodiment 2

The composition according to specific embodiment 1, wherein said composition comprises one α-hydroxy acid.

Specific Embodiment 3

The composition according to specific embodiment 1 or 2, wherein the glycerin phase of said emulsion has an apparent pH within 0.5 pH units of the $pK_a$ of said α-hydroxy acid.

Specific Embodiment 4

The composition according to any one of specific embodiments 1-3, wherein said composition is capable of existing as a solid stick for at least four weeks following solidification at 120° F. and 90% humidity.

Specific Embodiment 5

The composition according to any one of specific embodiments 1-4, wherein said α-hydroxy acid is lactic acid.

Specific Embodiment 6

The composition according to any one of specific embodiments 1-5, further comprising a composite elastomeric powder.

Specific Embodiment 7

The composition according to specific embodiment 6, wherein said elastomeric powder is a silicone elastomeric powder.

Specific Embodiment 8

The composition according to specific embodiment 6, wherein said elastomeric powder comprises dimethicone/vinyl dimethicone crosspolymer.

Specific Embodiment 9

The composition according to any one of specific embodiments 6-8, wherein said composite elastomeric powder is surface coated with inorganic particulates and/or one or more alcohols (e.g. monohydric alcohols, polyhydric alcohols, glycols, etc.).

Specific Embodiment 10

The composition according to specific embodiment 6, wherein said composite elastomeric powder is dimethicone/vinyl dimethicone crosspolymer (and) silica (and) butylene glycol.

Specific Embodiment 11

The lip composition according to any one of specific embodiments 6-10, wherein said composite elastomeric powder is present in an amount of 0.1-10% by weight of the composition.

Specific Embodiment 12

The lip composition according to any one of specific embodiments 6-10, wherein said composite elastomeric powder is present in an amount of 1% to 5% by weight of the composition.

Specific Embodiment 13

The lip composition according to any one of specific embodiments 1-12, wherein said composition comprises:

(a) between 1% and 45% glycerin by weight of the composition;
(b) between 40% and 95% oil by weight of the composition;
(c) between 1% and 10% α-hydroxy acid by weight of the composition; and
(d) between 1% and 10% elastomeric powder by weight of the composition.

Specific Embodiment 14

A method of providing therapeutic and/or cosmetic benefit to lips in need thereof comprising applying the lip composition according to any one of specific embodiments 1-13.

Specific Embodiment 15

The method according to specific embodiment 14, wherein said therapeutic and/or cosmetic benefit is selected from a reduction in water loss from said lips, smoother lip surface (as compared to untreated lips), increased moisture of said lips (as compared to untreated lips), increased barrier function of said lips (as compared to untreated lips), thickened stratum corneum of said lips (as compared to untreated lips), and combinations thereof.

Specific Embodiment 16

The method according to specific embodiment 14 or 15, wherein said composition is applied one or more times daily.

As various changes can be made in the above-described subject matter without departing from the scope and spirit of the present invention, it is intended that all subject matter contained in the above description, or defined in the appended claims, be interpreted as descriptive and illustrative of the present invention. Many modifications and variations of the present invention are possible considering the above teachings. Accordingly, the present description is intended to embrace all such alternatives, modifications and variances which fall within the scope of the appended claims.

The invention claimed is:

1. A lip composition in the form of a glycerin-in-oil emulsion comprising one or more α-hydroxy acids and a composite elastomeric particle.

2. The lip composition according to claim 1, wherein said composition comprises one α-hydroxy acid.

3. The lip composition according to claim 2, wherein the glycerin phase of said emulsion has an apparent pH within 0.5 pH units of the $pK_a$ of said α-hydroxy acid.

4. The lip composition according to claim 1, wherein said composition is capable of existing as a solid stick for at least four weeks following solidification at 120° F. and 90% humidity.

5. The lip composition according to claim 1, wherein one of said one or more α-hydroxy acids is lactic acid.

6. The lip composition according to claim 1, wherein said glycerin-in-oil emulsion is a solid emulsion; and said composite elastomeric particle is included in the composition to increase the stability of the solid emulsion as compared to an otherwise identical solid emulsion not containing the composite elastomeric particle.

7. The lip composition according to claim 1, wherein said composite elastomeric particle is a silicone elastomeric powder.

8. The lip composition according to claim 1, wherein said composite elastomeric particle comprises dimethicone/vinyl dimethicone crosspolymer.

9. The lip composition according to claim 1, wherein said composite elastomeric particle is surface coated with inorganic particulates and/or one or more alcohols.

10. The lip composition according to claim 1, wherein said composite elastomeric particle is dimethicone/vinyl dimethicone crosspolymer (and) silica (and) butylene glycol.

11. The lip composition according to claim 1 wherein said composite elastomeric particle is present in an amount of 0.1-10% by weight of the composition.

12. The lip composition according to claim 1, wherein said composite elastomeric particle is present in an amount of 1% to 5% by weight of the composition.

13. The lip composition according to claim 1, wherein said composition comprises:
(a) between 1% and 45% glycerin by weight of the composition;
(b) between 40% and 95% oil by weight of the composition;
(c) between 1% and 10% α-hydroxy acid by weight of the composition; and
(d) between 1% and 10% composite elastomeric particle by weight of the composition.

14. The lip composition according to claim 1, wherein the glycerin phase has a first normal stress difference of less than 20 Pa at a shear rate of 100 Pa and a temperature of 25° C.

15. A method of providing therapeutic and/or cosmetic benefit to lips in need thereof comprising applying the lip composition according to claim 1.

16. The method according to claim 15, wherein said therapeutic and/or cosmetic benefit is selected from a reduction in water loss from said lips, smoother lip surface as compared to untreated lips, increased moisture of said lips as compared to untreated lips, increased barrier function of said lips as compared to untreated lips, thickened stratum corneum of said lips as compared to untreated lips, and combinations thereof.

17. The method according to claim 15, wherein said composition is applied one or more times daily.

* * * * *